United States Patent [19]

Kiesewetter et al.

[11] Patent Number: 4,547,735
[45] Date of Patent: Oct. 15, 1985

[54] INSTRUMENT FOR MEASURING THE HEMATOCRIT VALUE OF BLOOD

[75] Inventors: Holger Kiesewetter, Schneebergweg 211, 5100 Aachen, Fed. Rep. of Germany; Heinz Myrenne, Roetgen, Fed. Rep. of Germany; Hartmut Lazar; Klaus Mussler, both of Aachen, Fed. Rep. of Germany

[73] Assignee: Holger Kiesewetter, Munich, Fed. Rep. of Germany

[21] Appl. No.: 460,565

[22] Filed: Jan. 24, 1983

[30] Foreign Application Priority Data

Jan. 25, 1982 [DE] Fed. Rep. of Germany ....... 3202067

[51] Int. Cl.[4] ............................................. G01N 27/28
[52] U.S. Cl. .................................. 324/450; 324/442; 324/447
[58] Field of Search ................ 324/71.1, 71.4, 439, 324/442, 425, 447, 450, 62 R; 204/403, 400

[56] References Cited

U.S. PATENT DOCUMENTS

| 3,648,160 | 3/1972 | Beaver | 324/442 |
| 3,689,393 | 9/1972 | Davis | 204/1 T |
| 3,922,598 | 11/1975 | Steuer et al. | 324/442 |
| 4,301,412 | 11/1981 | Hill et al. | 324/442 |

FOREIGN PATENT DOCUMENTS

| 1229760 | 12/1966 | Fed. Rep. of Germany. |
| 2103285 | 8/1971 | Fed. Rep. of Germany. |
| 78307 | 12/1970 | German Democratic Rep. |

Primary Examiner—Ernest F. Karlsen
Assistant Examiner—Kevin D. O'Shea
Attorney, Agent, or Firm—Poms, Smith, Lande & Rose

[57] ABSTRACT

The new instrument for taking readings of the hematocrit value from a blood sample has two electrodes with which the conductivity of the sample may be measured. The sample contacting faces of the electrodes are placed in a horizontal plane with an accurately fixed spacing therebetween so that a blood column of a given size may be formed from the sample. The sample is acted upon by ac. From a reading representative of the change in impedance the hematocrit value may be read off from a calibration curve.

15 Claims, 5 Drawing Figures

INSTRUMENT FOR MEASURING THE HEMATOCRIT VALUE OF BLOOD

BACKGROUND OF THE INVENTION

The present invention is with respect to an instrument for measuring the hematocrit value between two electrodes, whose acting faces are in horizontal planes and which may be used for measuring the conductivity of blood.

An apparatus on these general lines is to be seen in the East German Pat. No. 78,307, in which the electrodes are so placed that the field lines are normal to the direction of sedimentation of the blood, this however being generally a shortcoming insofar as the impedance value is dependent on the degree of sedimentation and the instrument error becomes greater with every increase in the sedimentation rate. This is more specially a shortcoming in the case of pathological blood samples in which the aggregation rate is greater than in normal blood.

On working with such an instrument it is not possible to make a simple correction of a reading that has been falsified by the effect of sedimentation, because such a correction operation would be over-complex.

Furthermore under working conditions it is likely for the electrodes in the sample chamber not to be completely clean and to have layers of protein, more specially fibrinogen, formed on them causing false readings for the impedance and for this reason the hematocrit value itself.

A further shortcoming of this known instrument is the trouble in handling it under working conditions. When the laboratory technician puts the precision capillary tubes between the clamps there is a loss in part of the blood from the tubes so that the readings are inaccurate, such loss of blood in fact causing the presence of air pockets that are responsible for a great increase in the impedance value. And furthermore the lost blood has the effect of dirtying the apparatus and producing errors.

Moreover because the instrument is not accurately filled there will be a scatter of the readings taken dependent on such volumes of filling, this being because the field line density in the blood is highly dependent on the volume filled.

In a further known instrument for measuring the hematocrit value, see German Auslegeschrift specification No. 1,229,760, the field lines produced by the electrode system are again normal to the direction of sedimentation so that there are likely to be the same trouble conditions in connection with taking readings as noted in connection with the apparatus of the East German patent.

Cleaning the electrodes is no simpler so that there are the same trouble conditions as with the first-noted form of instrument.

A further point in this connection is that the reading of the instrument is based on there being a linear dependence between the impedance and the hematocrit value that is not in fact in existence so that the translation of the readings is based on a false premise.

Lastly the sample temperature is not able to be kept constant because there is no thermostat, and this again is likely to make the readings inaccurate.

A further instrument for measuring the hematocrit level is to be seen in German Offenlegungsschrift specification No. 2,103,285, in which once again the field lines are normal to the direction the sedimentation so that the same troubles are noted hereinbefore are likely when taking readings. Furthermore large samples of blood are necessary for operation of the instrument. The electrodes may not be taken out for cleaning and for this reason there is likely to be trouble with contamination as noted earlier.

The U.S. Pat. No. 3,922,598 is with respect to a hematocrit measuring instrument in which again the field lines are normal to the direction of sedimentation, although in a further possible development of the instrument the electrodes are placed parallel over each other and may be dipped into the blood sample. In this case the depth of such dipping will not be constant because of the building up of sediment on the floor of the measuring chamber.

A further shortcoming is the overly large size of the volume in which measuring takes place on using the electrodes and there is trouble with cleaning the electrodes so that inaccurate readings are likely for the reasons noted hereinbefore.

GENERAL OUTLINE OF THE INVENTION

For these reasons one purpose of the invention is that designing a new instrument of the sort noted at the start of the present specification in which sedimentation is generally without any effect on the readings taken.

A still further purpose of the invention is that of designing an instrument that is simply and readily handled and used and, more specially, may be simply cleaned.

For effecting these and still further purposes or objects, an apparatus in keeping with the teachings of the present invention has lower and upper parts that may be separated and there is at least one electrode in the plane of the lower side and at least one electrode in the plane of the upper side.

By so placing the electrodes in the apparatus in keeping with the invention the field lines are lined up with the direction of sedimentation. A large number of tests undertaken on healthy and pathological (that is to say strongly sedimenting or aggregating) blood samples has made it clear that by placing the electrodes in this way, the sedimentation has hardly any effect on the readings, that is to say, the readings are accurate.

Because the electrodes are placed in the planes of the lower side and of the upper side, it is further possible to make certain that the measuring chamber may be completely and simply cleaned so that inaccurate readings otherwise caused by contamination or fouling of the electrodes are cut down as far as possible.

Furthermore only quite small blood samples are needed for getting highly accurate hematocrit values. In this respect filling the blood sample into the instrument is very simple. The amount of such a blood sample may be for example be 70 to 200 microliters. Such amounts, that is to say equal to roughly one to three drops of blood, may be taken from more or less any point of the patient's body.

By making a visual check it is possible to see at once if the blood, after wetting the lower end electrode has air bubbles in it on filling. Such bubbles would be the cause of the reading for the hematocrit being very much higher than the true value. In this case a second reading would be necessary.

Furthermore because of the very short measuring time no special processing of the blood as for example by mixing it with anti-coagulants is needed so that the measuring operation may be started once the droplet of blood has been put on the electrode.

The only point in this connection to be kept in mind is that there is a certain lower limit to the amount of the blood sample to be filled into the apparatus, the electrodes being so positioned in the chamber that one may be certain of having the same size of sample each time. If one keeps to these conditions and if the two electrodes are fully wetted, it is possible to make certain that the reading is not dependent on the amount that has been filled into the instrument. This has in fact been proved by experiments.

The measuring operation may then be started, because an electrical connection has been produced between the two electrodes and the drop of blood.

In the invention the preferred frequency of the current used in the instrument is 2 to 3 kHz, this putting an end to or suppressing polarisation effects at the electrodes. Furthermore this frequency takes into account the dielectric properties of the plasma as a coarsely-dispersed solution of large dipole molecules. In point of fact this frequency range is clear of the frequency range in which there is alpha-dispersion. In this range cell membranes are responsible for playing the most important part as conductor elements. On the other hand the said range comes within the range in which beta-despersion is starting and the dielectric property of the plasma still has a small effect on the reading. By such selection of the frequency range or value it is possible to make certain that the impedance values of normal and of pathological plasma (in which the protein concentration level has been changed from the normal value) are more or less the same. Furthermore the selection of the frequencies in question is such that the effect of the capacitive resistance of the erythrocyte membrane is suppressed to such a degree that even changes in the average corpuscular volume as large as 25% are without effect on the reading.

It has been seen from tests that for hematocrit values of up to 70% the reading is not dependent on the volume being in the form of a small number of large-volume cells or of a larger number of smaller-volume cells.

By the selection of these limiting conditions, changes in the osmotic pressure within the physiological range (that is to say 280 to 300 mosmoles) are only responsible for a change in the impedance of the plasma of roughly 10%, this causing an error of the hot value of ±1%.

It has been seen in the development of the present invention that the hematocrit value may be measured in a very short time, that is to say in a time of the order of half a minute and that the reading is stable and reproducible. A comparison with measuring operations of the prior art has furthermore made it clear that the readings taken are highly accurate and there is no trouble with systematic errors, seeing that in addition to placing a drop of blood on the electrode and more specially seeing that the electrode surface is completely covered with the sample, no further operations are necessary before taking the reading. Such work may readily be undertaken by an laboratory technician without any special training. Because all the characteristics of the instrument that are important for taking readings (such as the spacing of the electrodes, the frequency of the constant voltage oscillator, the resistance values, the calibration curve etc.) may be adjusted by the maker, the instrument may readily be used by a general practitioner and the use thereof is in no way limited to a medical laboratory.

Even if there are stiffened cells in the sample, an accurate hematocrit reading may be produced, that is to say the measuring operation is not in any way changed by the presence of such cells, something that may not be said for most of the prior art instruments.

A fact that is more specially important is that the sedimentation of the cellular components of a blood sample do not have any effect on measuring the hematocrit value and the readings will be the same and stable even if taken over periods of some minutes.

Further details and useful effects of the invention will be seen from the account now to be given of one working example using the FIGS. 1 to 5 hereof.

LIST OF DIFFERENT VIEWS OF THE FIGURES

DETAILED ACCOUNT OF WORKING EXAMPLE OF THE PRESENT INVENTION

Figure 1:
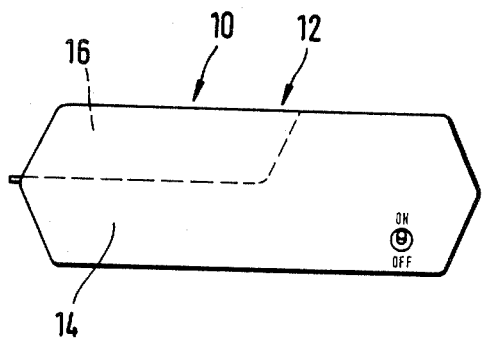
FIG. 1 is a diagrammatic side view of an instrument keeping to the teachings of the present invention.
Figure 2:
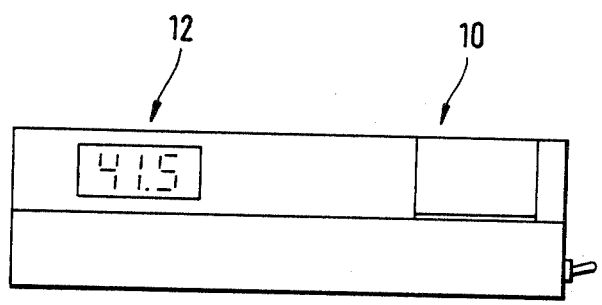
FIG. 2 is a diagrammatic end-on view of the instrument of the invention.
Figure 3:
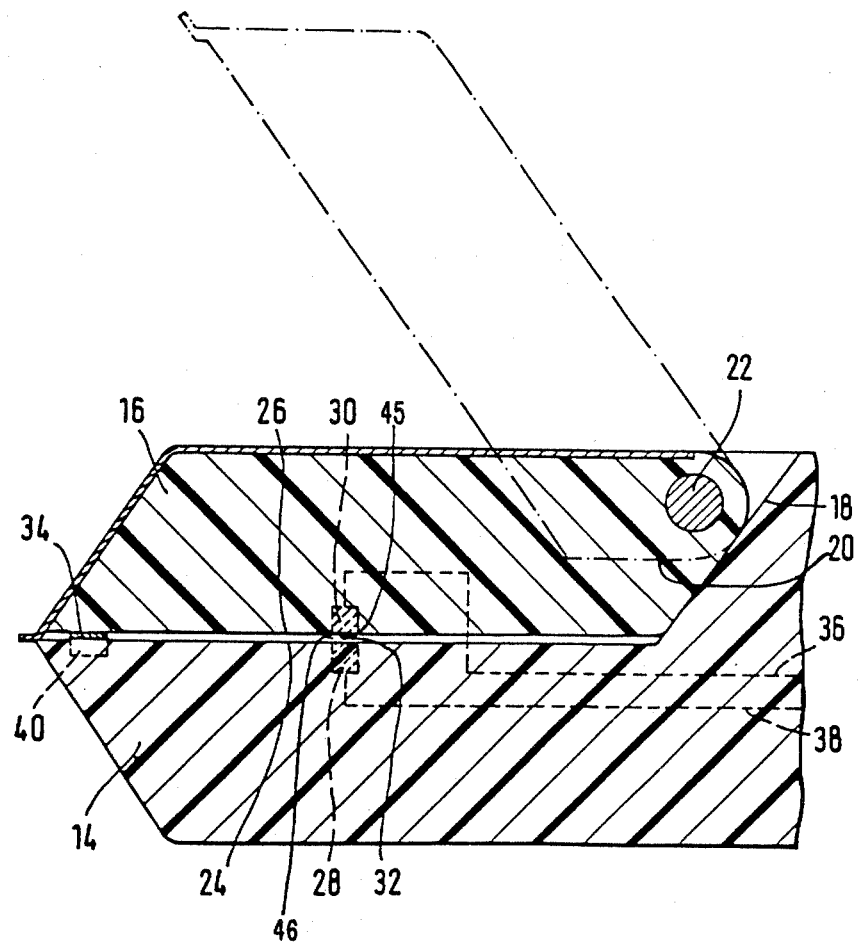
FIG. 3 is a view of part of the instrument of FIGS. 1 and 2 on a larger scale.
Figure 4:
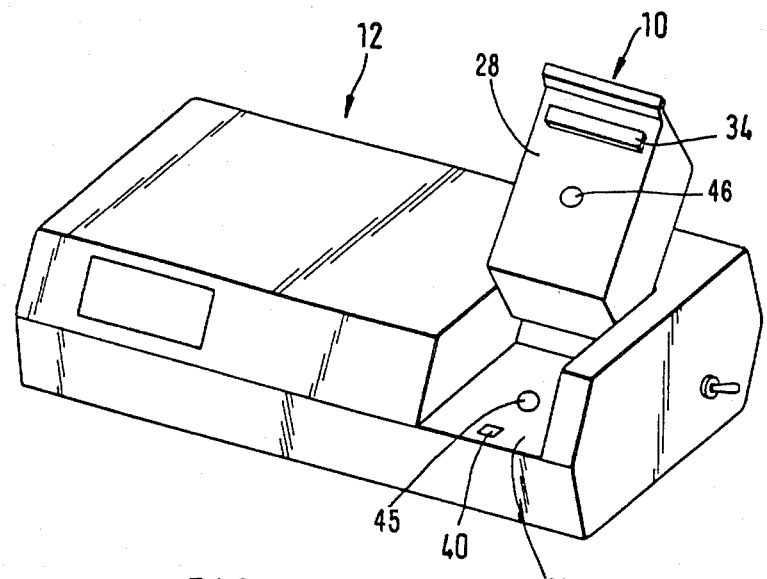
FIG. 4 is a diagrammatic view of the instrument of FIGS. 1 and 2 as seen at an angle.

In FIGS. 1 to 4 the reader will see different views of the instrument of the present invention for measuring the hematocrit value in blood, together with a recording unit 12 placed in a common housing therewith. The instrument 10 has as its main parts a lower half or part 14 and an upper part 16, that is hinged to the lower part 14 like a sort of cover. In the view of FIG. 3 of part of the instrument the folded-open position of the upper part 16 is marked in chained lines. The opening motion of the upper part 16 is limited by its coming to rest against a sloping face 18 on the lower part 14, or the upper part 16 may jammed in position at 20 on the sloping face 18. As we have seen, the upper part 16 may be turned about a turnpin 22, that is taken up in holes in the lower part 14 and the upper part 16.

The topside 24 of the lower part 14 and the lower side 26 of the top or upper part 16 each have one electrode, that is to say 28 in the one and 30 in the other case, whose surfaces are in the same plane as the upper side 24 and the lower side 26. This is responsible for the useful effect that on carefully cleaning the full upper and lower sides one may be certain that electrodes are completely cleaned as well without any dirt or contaminant still being on the surfaces, that might otherwise be responsible for the instrument giving inaccurate readings. On the other hand it it may in some cases be best for the electrodes 28 and 30 to be recessed into the surfaces or to protrude therefrom, for example by 1 to 2 mm.

The form and size of the electrode surfaces is not a question of key importance. It will however be best to have a round form of surface to the electrodes seeing that they are to be wetted as far as possible with the blood, and this would not be so readily possible if the surfaces were to be made running out into corners. Furthermore the size of the surfaces 45 and 46 of the electrodes 28 and 30 is to be such that the sample signal may be safely recorded or registered with a good signal to noise ratio, while on the other hand not needing overly large amounts of blood to make this possible. Normally the sizes of the surfaces of the electrodes 28 and 30 will be in a range of 10-100 and more specially 20 to 50 sq. mm.

In a more specially useful, preferred form of the invention the electrode area is about 30 sq. mm.

Furthermore the maker of the instrument has a wide selection with respect to the material of the electrodes 28 and 30. It is only necessary to see that the material has a good electrical conductivity, is resistant to corrosion and does not take part in any reaction with the blood. It has been seen from tests that most normally-used electrode materials such as titanium, nickel, stainless steel, chromium and noble metals such as platinum, silver and gold may well be used without any undesired effects. For reasons of price stainless steel is the preferred electrode material.

As the reader will see from FIG. 3, the two electrodes 28 and 30 are placed truly over each other, or to put it differently, one electrode is the vertical projection of the other, so that in the space 32 therebetween a column of blood may be formed as the sample whose electrical conductivity is to be measured. The size of the space 32 between the electrodes is dependent on the positioning of the upper and lower parts 14 and 16 as fixed more specially by a stop 34 acting as a spacer between the upper side 24 and the lower side 26. In this respect the upper side 24 and lower side 26 are generally parallel to each other in the shut position of the instrument so that the surfaces of the electrodes 28 and 30 will be parallel to each other was well.

It has been seen from tests that the distance between the electrodes 28 and 30, that is to say the height of the inbetween space 32 and for this reason the thickness of the stop 34 as well may be in a range of about 0.5 to 3 and more specially 1.4 to 2.2 mm. Working in this distance range with the electrode areas as noted, there is a wide distribution of the measuring range so that amounts of blood of 500 microliters at the most are all that are needed for measuring the hematocrit level.

As a material for the upper and lower sides 24 and 26 non-conductors are used, inasfar as such materials are used next to, and touching the electrodes 28 and 30. However if the materials are insulated from the electrodes 28 and 30, metals may be used. Normally one will have a thermoplastic synthetic material or normal housing material for the instrument 10.

The electrodes 28 and 30 are joined up by way of wires 36 and 38 with the recording unit 12. The recording unit is best so placed in circuit that it is automatically put into operation when a limit switch 40 is turned on when the upper part 16 is folded down onto the lower part 16. It is best for the limit switch 40 to be worked by the stop 34 on the upper part 16. The connections joining the limit switch 40 with the recording 12 unit are not to be seen in the figures.

The electrodes 28 and 30 are supplied with ac. having for example an rms value of 0.1 to 0.7 and more specially 0.2 V (2 V in the case of 0.7 rms.) and with a frequency of 1.8 to 6 and more specially 2 to 3 kHz.

Using the given frequency in the 2 to 3 kHz range polarisation effects at the electrodes are suppressed and furthermore at such a frequency the dielectric property of the plasma as a coarsely dispersed solution of large dipole molecules is taken into account and for this reason the cell membranes do not have the effect of conductor elements. On the other hand this frequency comes within a range in which the dielectric property of the plasma still has a small effect on the reading. Because of the selection of the preferred frequency range it is possible to make certain that not only the impedance value of normal plasma but furthermore that of pathological plasma, in which the protein concentration is unchanged, is more or less the same. Furthermore by the selection of the frequencies as noted hereinbefore the effect of the capacitive resistance of the erythrocytes membrane is so cut down that even changes in the average corpuscular volume of the erythrocytes of 25% do not make the readings inaccurate.

It has been seen from testing that up to hct values of 70% the reading is independent of the volume percentage of the cells with small and large volumes.

Figure 5:
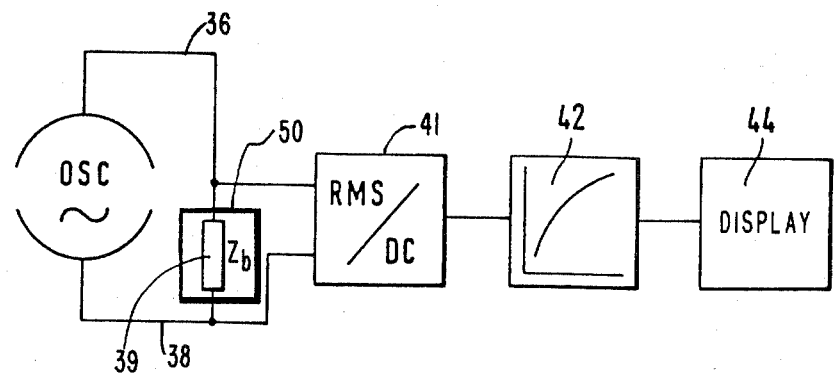
FIG. 5 is an electrical schematic with a constant current supply unit for the instrument.

As shown schematically in FIG. 5, an oscillator, operating at a voltage and frequency referenced above, is connected by conductors 36 and 38 to the electrodes 28 and 30, whose contact surfaces 45 and 46 then apply the potential to the two ends of the cylinder of blood sample (shown schematically at 39) present within space 32 whose conductivity (or its reciprocal, the impedance $Z_b$) is to be measured. The RMS value of the current through the sample, or the voltage drop across it is then measured and rectified in block 41 into a DC signal that is proportional to the conductivity of the sample. This signal is then compared to known values of hematocrit on a calibration curve in block 42 and converted to a rating for the hematocrit level. (An account of a method for setting up the calibration curve will be given hereinafter). The hematocrit reading is then displayed at a readout or display 44, preferably of digital design, which is part of the recording unit 12.

The instrument 10 and the recording unit 12 may be in the form of two separate units.

An account will now be given of the taking of a reading for the hematocrit value of the blood.

With the cover 16 in the open position, a sample of about 200 microliters of blood is placed on the upper surface 24 in the area which includes the contact surface 45 of the lower electrode 28, care being taken to verify that the contact surface is completely wetted with the blood and that there are no air bubbles present in the sample. The blood may be taken from any point on the patient's body that is readily got at, as for example from the part of the finger between the nail and the most distal finger joint using a needle and letting off the drops of blood directly onto the lower electrode 28. Nextly the upper part 16 is folded down onto the lower part 14 and the limit switch 40 is turned on. After turning on the power supply it will take about 15 seconds before the reading for the voltage drop gets to a steady level. This voltage drop is more importantly dependent on the impedance, that is to say the ac. resistance, of the erythrocytes and it is correlated with the hematocrit value using the calibration curve. Seeing that the osmotic pressure, or osmularity, that is to say the electrolyte charge units, is one of the best controlled factors in the blood circulation, its effects are practically negligible. The capacitive resistance of the blood plasma and the ohmic and capacitive resistance of the erythrocytes are as well much less important in taking the readings, it having been seen from tests that they may be taken to be constant and for this reason do not have to be taken into account.

The voltage value or signal supplied to the recording unit 12 is naturally dependent on the temperature, the ion concentration in the suspension medium, the electrode spacing and to a certain degree on the volume of sample filled into the sample chamber as well. As pointed out at an earlier stage, the electrode spacing and the volume of sample filled thereinto and which is the product of the spacing and the electrode area, are constant, if the electrode areas are completely covered by the blood. In a preferred form of the instrument, to make certain that the electrodes 30 and 28 are completely covered, they have a safety margin round their outer edges, that has to be covered with blood when the instrument is opened up by the laboratory technician using it.

As noted, the osmotic pressure of the plasma is of lesser importance for the accuracy of the hematocrit reading. It is between values of roughly 275 and 300 mosmoles/l. The error in the hematocrit (Deltahct) is then ±1% volume, so that in the case of a normal hematocrit value of 40% by volume it will be of the order of about 2.5%. For this reason no dummy measurement on the plasma is necessary. However the conductivity of the plasma may be measured in the same chamber. If necessary a correction will be made or the instrument may be calibrated using a standard NaCl solution.

The hematocrit readings are naturally temperature dependent and for each different temperature a different calibration curve is needed. In this respect it is useful if the instrument 10 is used with a thermostat or other conventional temperature control device such as heater 50 shown diagramatically in FIG. 5. for automatically controlling its temperature. Such thermostat operation of the instrument may be undertaken in the usual way, e.g., by placing a resistive heater $R_h$ switched by a thermostat, both in close proximity to the sample measuring area.

If readings are taken at room temperature it is best for the impedance to be measured using a reference solution that has first been tempered to be at room temperature. The reading then taken for the blood at the same temperature will then have to be corrected, something that may best be done by compensation of the potential using a potentiometer in the recording unit 12. Working under such conditions it may then even be possible to do without tempering the blood, this being because even changes of ±3 degrees C. at a given room temperature of roughly 295 degrees K. will only be responsible for an error (Deltahct) of ±1% vol.

COMPARISON TEST

Erythrocytes were stiffened with 5 mmoles/l diamide, adjustment of the hct value to 0.35 to 0.51 being undertaken by a centrifuging method. Nextly the hematocrit value was measured using the impedance instrument in keeping with the present invention and furthermore using the $^{14}C$-saccharose method. From the readings produced it was possible to see that there was a 1 to 1 correlation between the two last-named methods, the readings produced in the two cases being about 32.4 and 46.0. The reading produced by centrifuging was 6 to 7% (hct=0.35) and 10 to 11% (hct=0.51) higher than these readings.

Generally speaking the apparatus of the present invention makes it possible to take readings for the hematocrit value within a range of 0 to 80% vol. If the instruments is made fully automatic operation is simple. The overall time for measuring a sample is less than 30 seconds. Furthermore using the method the patient is hardly distressed at all in view of the small amount of blood (about 70 to 200 microliters) needed.

We claim:

1. An apparatus for measuring the hematocrit value of a blood sample comprising:
    an upper electrode having a sample contact surface;
    a lower electrode having a sample contact surface which is substantially the same size and shape as said upper electrode contact surface;
    means for selectively moving the electrodes between a blood sample measurement position and a second position where said electrodes are displaced away from each other to facilitate cleaning of the electrode faces and introduction of blood samples onto the electrode faces and wherein said electrode faces in said sample measurement position are substantially parallel with said upper electrode face being located directly above said lower electrode face at a spaced distance from said lower electrode face such that a blood sample defining a cylindrical column having a vertical axis may be formed between said upper and lower electrode faces, said electrode faces being oriented such that sedimentation of said blood sample occurs along the vertical axis of said blood sample column; and
    conductometry means connected to said electrodes for measuring the hematocrit value of the blood sample.

2. The apparatus as recited in claim 1 wherein the means for moving the electrodes comprises:
    a fixed base having a substantially horizontal, planar upper surface mounting said lower electrode such that the contact surface of the lower electrode faces upward and is substantially parallel with the base's upper surface and upon which the sample to be measured may be placed;
    a movable cover having a substantially planar, lower surface mounting said upper electrode such that the contact surface of the upper electrode faces downward and is substantially parallel with the cover's lower surface; and,
    hinge means which rotatably connects the cover to the base for raising and lowering the cover with respect to the base to move the electrodes between said sample measurement position and said second position.

3. An apparatus is recited in claim 1 one wherein the conductometry means comprises:
    an oscillator means for applying an alternating voltage to the upper and lower electrodes;
    means for measuring the conductivity of the blood sample column located between the upper and lower electrodes and converting its value into a DC signal that is proportional to the conductivity;
    means for comparing the conductivity value to those of known samples and converting the value into a reading for the hematocrit; and means for displaying the hematocrit value measured.

4. The apparatus as recited in claim 1 wherein said electrode contact surfaces are substantially circular in aspect and have an area of from 10 to 100 SQ. MM.

5. The apparatus as claimed in claim 4 wherein said area is generally between 20 and 50 sq. mm.

6. The apparatus as recited in claim 1 wherein the electrodes consist of a material that is electrically conductive, non-corrosive and non-reactive with blood.

7. The apparatus as recited in claim 6 wherein the electrodes are made from a metal selected from the following group: platinum, silver, gold, titanium, nickel, stainless steel and chromium.

8. The apparatus as recited in claim 1 wherein the electrodes are made from an electrically-conductive material and have sample contact surfaces that are plated with a material that is electrically-conductive, noncorrosive and non-reactive with blood.

9. The apparatus as recited in claim 1 wherein the electrode contact surfaces are plated with a metal selected from the following group: platinum, silver, gold, titanium, nickel, stainless steel and chromium.

10. The apparatus as recited in claim 1 wherein the fixed distance between the sample contact surfaces in said sample measurement position is from 0.5 to 3 mm.

11. The apparatus as recited in claim 10 wherein the fixed distance is from 1.4 to 2.2 mm.

12. The apparatus as recited in claim 2 further comprising switch means for activating the conductometry means when the cover is moved to said sample measurement position.

13. The apparatus as recited in claim 1 further comprising: means for controlling the temperature of the blood sample.

14. The apparatus as recited in claim 1 wherein the oscillator means supplies 0.1 to 0.7 Vac rms.

15. The apparatus as recited in claim 14 wherein the oscillator means operates at a frequency of from 1.8 to 6 kHz.

* * * * *

UNITED STATES PATENT AND TRADEMARK OFFICE
CERTIFICATE OF CORRECTION

PATENT NO. : 4,547,735
DATED : October 15, 1985
INVENTOR(S) : Kiesewetter, et al It is certified that error appears in the above-identified patent and that said Letters Patent are hereby corrected as shown below:

In the Foreign Application Data Field (Cover Page), the foreign priority date reading "Jan. 25, 1982" should read --Jan. 23, 1982--.
In column 8, line 47, "is" should read --as-- and "one" should be deleted.
In column 9, line 8, the claim reference 1 should read --8--.
In column 10, line 10, the claim reference "1" should read --3--.

Signed and Sealed this

Seventh Day of October, 1986

[SEAL]

Attest:

DONALD J. QUIGG

Attesting Officer

Commissioner of Patents and Trademarks